US012807609B2

(12) United States Patent
Rech et al.

(10) Patent No.: US 12,807,609 B2
(45) Date of Patent: Nov. 24, 2026

(54) SYNTHESIS OF EGFR MODULATORS

(71) Applicant: THE REGENTS OF THE UNIVERSITY OF MICHIGAN, Ann Arbor, MI (US)

(72) Inventors: Jason Christopher Rech, Ann Arbor, MI (US); Mukesh K. Nyati, Superior Township, MI (US); Fan Fang, Suzhou (CN); Lei Zhang, Suzhou (CN); Julian Paul Henschke, Uraidla (AU)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 491 days.

(21) Appl. No.: 18/031,219

(22) PCT Filed: Oct. 12, 2021

(86) PCT No.: PCT/US2021/054485
§ 371 (c)(1),
(2) Date: Apr. 11, 2023

(87) PCT Pub. No.: WO2022/081514
PCT Pub. Date: Apr. 21, 2022

(65) Prior Publication Data
US 2024/0018144 A1 Jan. 18, 2024

Related U.S. Application Data

(60) Provisional application No. 63/090,336, filed on Oct. 12, 2020.

(30) Foreign Application Priority Data

Oct. 12, 2020 (WO) ................ PCT/CN2020/120339

(51) Int. Cl.
*C07D 471/10* (2006.01)

(52) U.S. Cl.
CPC .................................. *C07D 471/10* (2013.01)

(58) Field of Classification Search
CPC .................................................... C07D 471/10
See application file for complete search history.

(56) References Cited

U.S. PATENT DOCUMENTS

| | | | | |
|---|---|---|---|---|
| 8,039,460 | B2 | 10/2011 | Burgey et al. | |
| 11,358,965 | B2 * | 6/2022 | Nyati | C07D 233/70 |
| 11,999,731 | B2 * | 6/2024 | Nyati | C07D 233/70 |
| 2016/0016956 | A1 | 1/2016 | Esaki et al. | |

FOREIGN PATENT DOCUMENTS

| | | | |
|---|---|---|---|
| WO | WO-2005/095398 | A1 | 10/2005 |
| WO | WO-2019122268 | A1 | 6/2019 |
| WO | WO-2019/165358 | A1 | 8/2019 |

OTHER PUBLICATIONS

Cheng et al., Versatile spirocyclic glycine-based nitrones and their highly stereoselective 1,3-dipolar cycloaddition, Synthetic Communications, 37(2):297-308 (2007).
International Application No. PCT/US2021/054485, International Search Report and Written Opinion, mailed Jan. 12, 2022.
First Examination Report for India Application No. 202317031668, dated Aug. 27, 2026.

* cited by examiner

*Primary Examiner* — John S Kenyon
*Assistant Examiner* — Rehana Ismail
(74) *Attorney, Agent, or Firm* — MARSHALL, GERSTEIN & BORUN LLP

(57) ABSTRACT

Provided herein are processes for synthesizing compounds useful as EGFR modulators. In particular, provided herein are processes for synthesizing Compound A:

(Compound A)

(I)

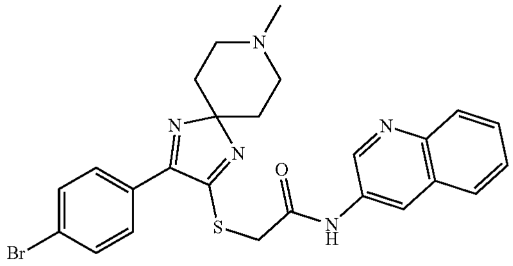

19 Claims, No Drawings

SYNTHESIS OF EGFR MODULATORS

BACKGROUND

The present disclosure relates to processes for synthesizing 2-((3-(4-bromophenyl)-8-methyl-1,4,8-triazaspiro[4.5]deca-1,3-dien-2-yl)thio)-N-(quinolin-3-yl)acetamide (Compound A) and salts thereof:

(A)

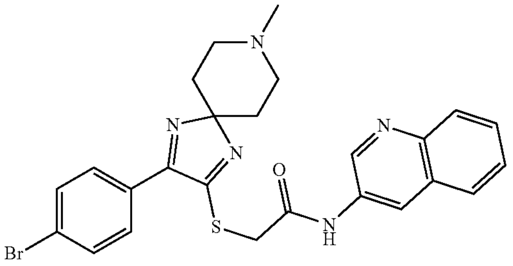

Compound A is a modulator of EGFR useful in treating or preventing diseases or disorders associated with aberrant EGFR activity, e.g., cancer.

The EGFR small molecule tyrosine kinase inhibitors (TKI's) erlotinib, gefitinib, and afatinib have been most successful as single agents in the treatment of lung adenocarcinomas that have somatic mutations (such as L858R or deletion in exon 19, i.e. E746-A750) that confer sensitivity to this class of drugs, which occur in 7-20% of patients depending on ethnicity and gender. Unfortunately, responses rarely last more than a year because virtually all patients develop resistance to therapy. A third-generation irreversible inhibitor, osimertinib (AZD9291), is effective in treating naïve as well as patients who have acquired resistance to first or second generation TKIs. However, within a year of treatment with osimertinib, a majority of patients develop another mutation in the EGFR kinase domain (C797S), which is the drug covalent attachment site. Although several approaches to target osimertinib resistant EGFR have been reported, as of now no TKI treatment option exists for these patients with this C797S mutation. Chemotherapy is the only option.

In view of the foregoing, there exists a need for a cancer therapeutic that targets EGFR in a manner other than inhibition of EGFR tyrosine kinase activity. There also exists a need for a therapeutic that treats cancer without drug resistance developing after initial use.

PCT Publication No. WO 2019/165358, which is incorporated herein by reference in its entirety, discloses compound A as an EGFR modulator and provides a process for preparing it. However, improved synthetic processes that result in greater yield and purity of Compound A are desired, particularly for the commercial production of compound A.

SUMMARY

Provided herein are processes for synthesizing Compound A, or a salt or solvate thereof:

(A)

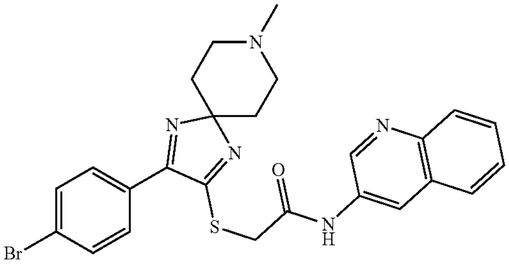

;

comprising (i) admixing Compound I and a halogenation reagent or a sulfonylation reagent to form Compound II:

(I)

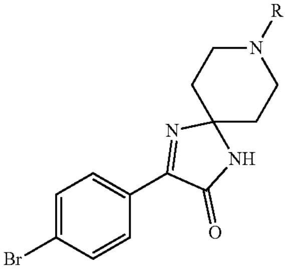

and (II)

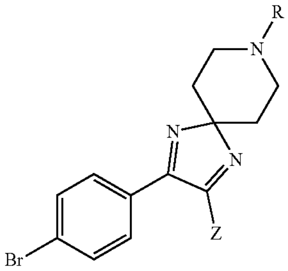

, wherein R is methyl or a nitrogen-protecting group and Z is a halogen or a sulfonate group. In some cases, R is methyl. In some cases, R is a nitrogen-protecting group. In some cases, R is t-butyloxycarbonyl (Boc), benzyloxycarbonyl (Cbz), benzyl, or p-methoxybenzyl (PMB). In some cases, Z is a sulfonate group. In some cases, the sulfonate group is triflate, mesylate, tosylate, benzenesulfonate, or nosylate. In some cases, the sulfonate group is triflate.

In some cases, Compound II is synthesized by admixing Compound I and a halogenation reagent. In some cases, the halogenation reagent is a chlorination reagent. In some cases, the chlorination reagent comprises oxalyl chloride, $SOCl_2$ or $POCl_3$.

In some cases, Compound II is synthesized by admixing Compound I and a sulfonylation reagent. In some cases, the sulfonylation reagent is selected from triflic anhydride, mesyl chloride, mesic anhydride, tosyl chloride, tosic anhydride, nosyl chloride, and a perfluoroalkylsulfonic anhydride. In some cases, the sulfonylation reagent is triflic anhydride.

In some cases, Compound II is synthesized by admixing Compound I and a halogenation or a sulfonylation reagent in an organic solvent. In some cases, Compound II is synthesized by admixing Compound I and a halogenation or a sulfonylation reagent in a mixture of organic solvents. In some cases, Compound II is synthesized by admixing Compound I and a halogenation or a sulfonylation reagent in a mixture of dichloromethane and ethyl acetate.

In various embodiments, the processes further comprise synthesizing Compound A by (ii) (a) admixing Compound II and Compound III in the presence of a base to form Compound A:

(III)

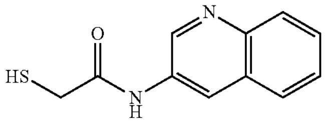

;

or (b) (I) admixing Compound II and a nucleophilic sulfuration reagent to form Compound IIA, then (II) admixing Compound IIA with Compound IIIA in the presence of a base to form Compound A:

(IIA)

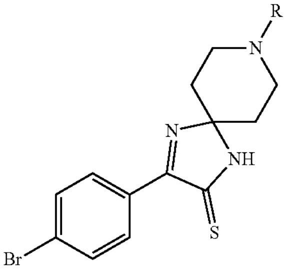

and (IIIA)

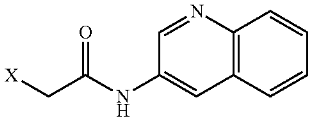

, wherein X is halogen.

In some cases, X is Br or Cl. In some cases, X is Cl.

In some cases, the processes comprise synthesizing Compound A by admixing Compound II and Compound III in the presence of a base to form Compound A. In some cases, the base is NaH, NaOH, KOH, sodium methoxide, sodium ethoxide, sodium tert-butoxide, or potassium tert-butoxide.

In some cases, the processes comprise synthesizing Compound A by (b) (I) admixing Compound II and a nucleophilic sulfuration reagent to form Compound IIA, then (II) admixing Compound IIA with Compound IIIA in the presence of a base to form Compound A. In some cases, the nucleophilic sulfuration reagent comprises $Li_2S$, $Na_2S$, $K_2S$, $Li_2S_x$, $Na_2S_x$, $K_2S_x$, (wherein x=2-5), $NaBH_4/S$, NaSH, AcSK, thiourea or a salt or hydrate thereof. In some cases, the nucleophilic sulfuration reagent comprises a hydrate of $Na_2S$. In some cases, the nucleophilic sulfuration reagent comprises $Na_2S{\cdot}4H_2O$.

In some cases, the processes comprise synthesizing Compound A by (b)(I) admixing Compound II and a nucleophilic sulfuration reagent in an organic solvent to form Compound IIA. In some cases, the processes comprise synthesizing Compound A by (b)(I) admixing Compound II and a nucleophilic sulfuration reagent in a mixture of organic solvents to form Compound IIA. In some cases the processes comprise synthesizing Compound A by (b)(I) admixing Compound II and a nucleophilic sulfuration reagent in a mixture of dichloromethane and ethyl acetate to form Compound IIA.

In some cases, the processes comprise synthesizing Compound A by (II) admixing Compound IIA with Compound IIIA in the presence of a base to form Compound A. In some cases, the base is $K_2CO_3$.

In some cases, the processes comprise synthesizing Compound A by (II) admixing Compound IIA with Compound IIIA in the presence of a base in an organic solvent to form Compound A. In some cases, the organic solvent is isopropanol.

In various embodiments, the processes further comprise synthesizing compound A by (iii) optionally, when R is a nitrogen-protecting group, removing the nitrogen-protecting group and methylating the resulting deprotected amine to form Compound A wherein R is methyl. In some cases, when the processes comprise step (iii), R is a nitrogen-protecting group. In some cases, step (iii) is performed between steps (ii)(b)(I) and (ii)(b)(II). In some cases, when R is a nitrogen-protecting group, the process further comprises removing the nitrogen-protecting group from Compound IIA and methylating the resulting deprotected amine to form Compound IIA wherein R is methyl. In some cases, removing the nitrogen-protecting group comprises admixing in the presence of acid. In some cases, the deprotected amine is methylated by admixing with $NaBH(OAc)_3$, $CH_2O$, and acetic acid.

Further aspects and advantages will be apparent to those of ordinary skill in the art from a review of the following detailed description. The description hereafter includes specific embodiments with the understanding that the disclosure is illustrative, and is not intended to limit the invention to the specific embodiments described herein.

DETAILED DESCRIPTION

Provided herein are processes for synthesizing EGFR modulators and salts thereof. In particular, processes for synthesizing 2-((3-(4-bromophenyl)-8-methyl-1,4,8-triazaspiro[4.5]deca-1,3-dien-2-yl)thio)-N-(quinolin-3-yl)acetamide (Compound A) and salts thereof are provided:

(A)

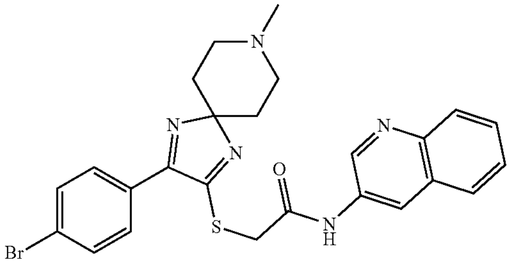

.

PCT Publication No. WO 2019/165358 (the "'358 application"), which is incorporated herein by reference in its entirety, discloses Compound A as an EGFR modulator and provides a process for preparing it.

The '358 application generally describes a procedure for making compounds such as Compound A as shown in Scheme 1, below, which is adapted from the disclosure at paragraph [0090] (General Procedure A) of the '358 application. The '358 application describes that substituted acetamides 7A-G were added to 3-(4-bromophenyl)-8-methyl-1,4,8-triazaspiro[4.5]dec-3-ene-2-thione (labeled as Compound 6) in anhydrous acetonitrile and warmed to 40° C. Next, 2M aqueous potassium carbonate solution was added to the reaction mixture and the reaction was maintained at 40° C. until TLC analysis indicated loss of starting materials and a new R f spot (typically 2-6 hours). By following the procedure in Scheme 1 using 2-chloroacetamides 7, substituted 3-(4-bromophenyl)-8-methyl-1,4,8-triazaspiro[4.5]deca-1,3-diene-2-thiols 8A-G were produced, including using 7C (2-chloro-N-quinolin-3-yl-acetamide) to produce Compound A (referred to as "8C" in the '358 application).

Scheme 1 - General Procedure A of the '358 Appliction

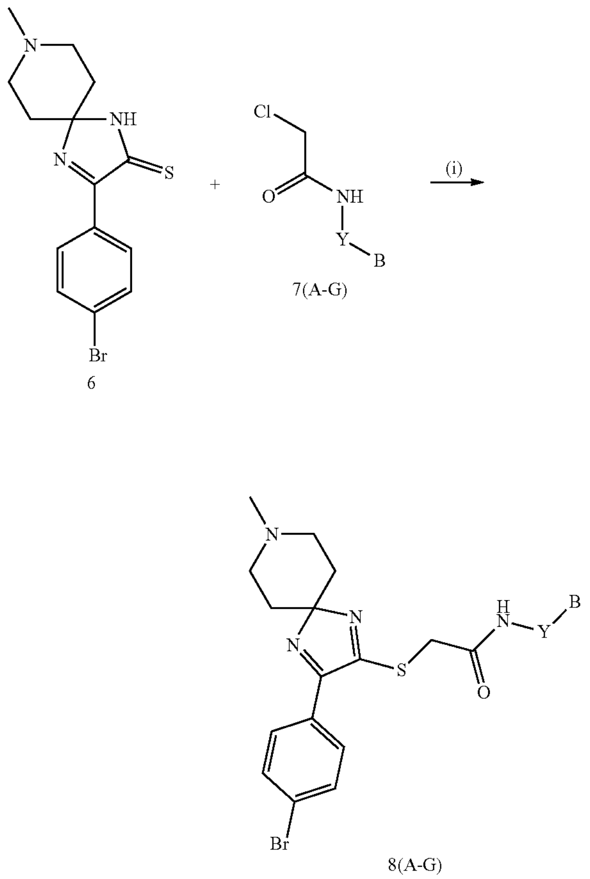

6

7(A-G)

8(A-G)

Reaction conditions: (i) 2M aq. $K_2CO_3$, Acetonitrile, 40° C.
Y: $C_{0-6}$alkylene
B: optionally substituted $C_{6-10}$ aryl, 5-10 membered heteroaryl, 3-8 membered cycloalkyl, or 3-12 membered heterocycloalkyl The '358 application further describes a process for synthesizing intermediate compounds like compound 6 in Scheme 1. Scheme 2, below, which is adapted from paragraph [0105] (Examples 15-28) of the '358 application, represents the general process of synthesizing substituted 2-(4-bromophenyl)-3-thioxo-1,4,8-triazaspiro[4.5]dec-1-ene compounds (e.g., compound 6) as described in the '358 application. Briefly, to a solution of tert-butyl 2-(4-bromophenyl)-3-thioxo-1,4,8-triazaspiro[4.5]dec-1-ene-8-carboxylate was added Lawesson's reagent in THF and the reaction mixture was heated to 60° C. until the reaction was complete by TLC. The reaction mixture was concentrated onto silica gel and purified by flash column chromatography (0-100% EtOAc in hexanes) to provide tert-butyl 2-(4-bromophenyl)-3-thioxo-1,4,8-triazaspiro[4.5]dec-1-ene-8-carboxylate.

Scheme2 - Synthesis of substituted 2-(4-bromophenyl)-3-thioxo-1,4,8-triazaspiro[4.5]dec-1-ene compounds of '358 Application

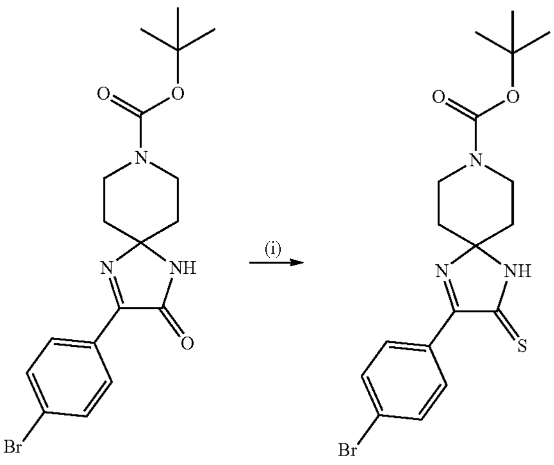

Reaction conditions: (i) Lawesson's Reagent, THF

The process of the '358 application has several disadvantages for large-scale synthesis. Significantly, the Lawesson's reagent used to convert the amide moiety to a thioamide is malodorous and highly moisture-sensitive, and there are potential difficulties in performing the amide to thioamide conversion at the scale of several hundred grams. The process of the '358 application also employs several column chromatography purification steps, which are impractical for a synthesis at the scale of several hundred grams or larger.

Advantageously, the processes described herein avoid the use of Lawesson's reagent for the preparation of thioamides, and are more practical and higher-yielding. The processes described herein also avoid the necessity of purification by column chromatography.

Described herein are processes for synthesizing Compound A and salts thereof:

(A)

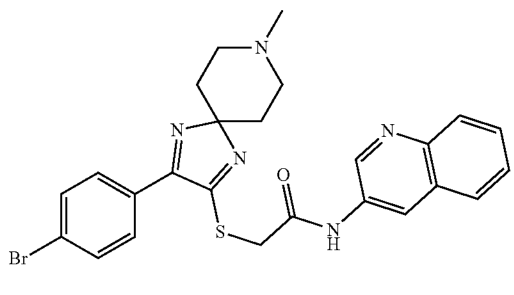
, comprising (i) admixing Compound I and a halogenation reagent or a sulfonylation reagent to form Compound II:

(I)

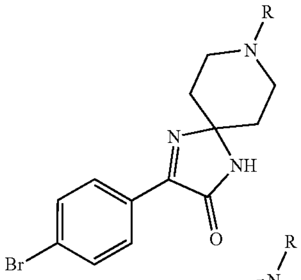

and (II)

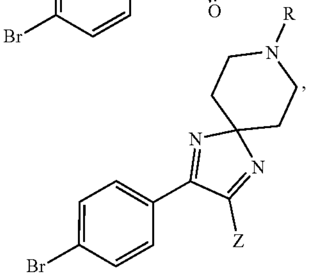

wherein R is methyl or a nitrogen-protecting group and Z is chloride or a sulfonate group;

(ii)

(a) admixing Compound II and Compound III in the presence of a base to form Compound A:

(III)

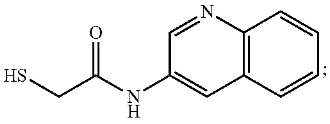

;

or (b) (I) admixing Compound II and a nucleophilic sulfuration reagent to form Compound IIA, then (II) admixing Compound IIA with Compound IIIA in the presence of a base to form Compound A:

(IIA)

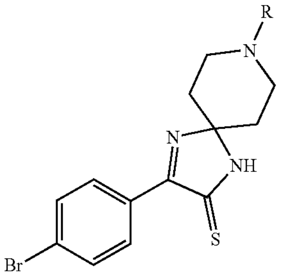

and (IIIA)

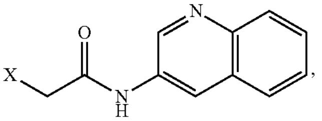

wherein X is Cl or Br, and (iii) optionally, when R is a nitrogen-protecting group, removing the nitrogen-protecting group and methylating the resulting deprotected amine to form Compound A wherein R is methyl, as discussed in detail below.

As will be appreciated, the disclosed processes involve formation of 3-(4-bromophenyl)-8-methyl-1,4,8-triazaspiro[4.5]deca-1,3-diene-2-thioacetamides by the addition of a thiol group to a 3-halo (e.g., 3-chloro)- or 3-sulfonyloxy-1,4,8-triazaspiro[4.5]deca-1,3-diene, or the addition of a chloro- or bromoacetamide to a 1,4,8-triazaspiro[4.5]dec-3-ene-2-thione.

A general reaction scheme for the processes described herein is provided in Scheme 3, below:

Scheme 3-General Process for Synthesis of Compound A

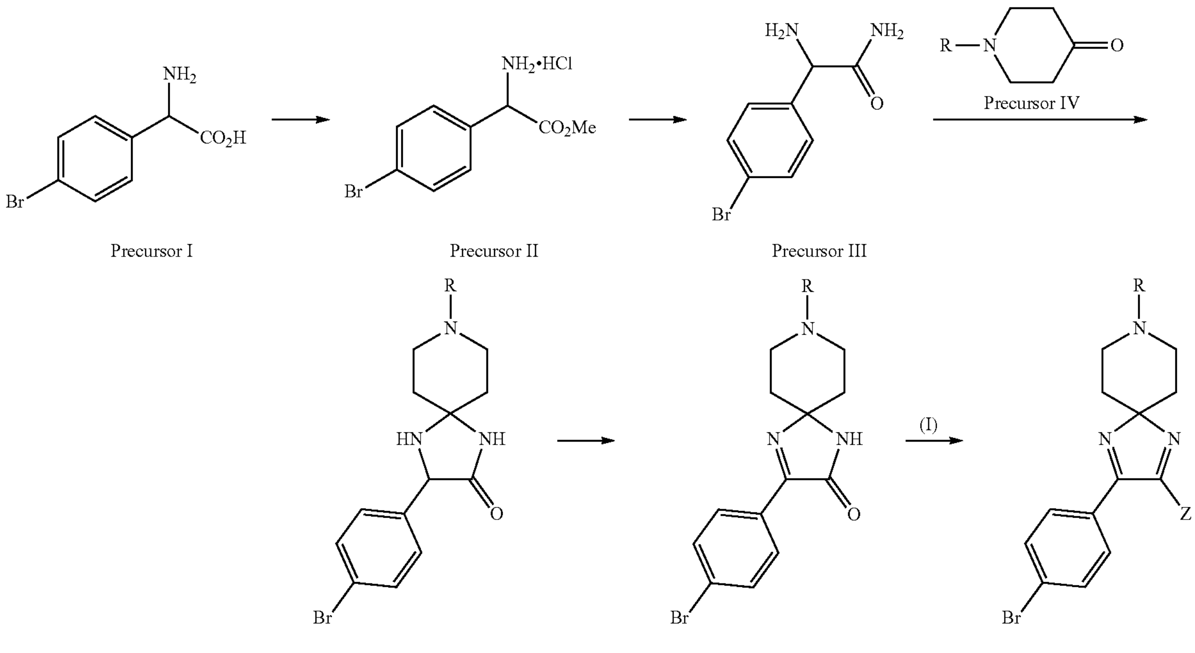

Precursor I

Precursor II

Precursor III

Precursor V

Compound I

Compound II

-continued

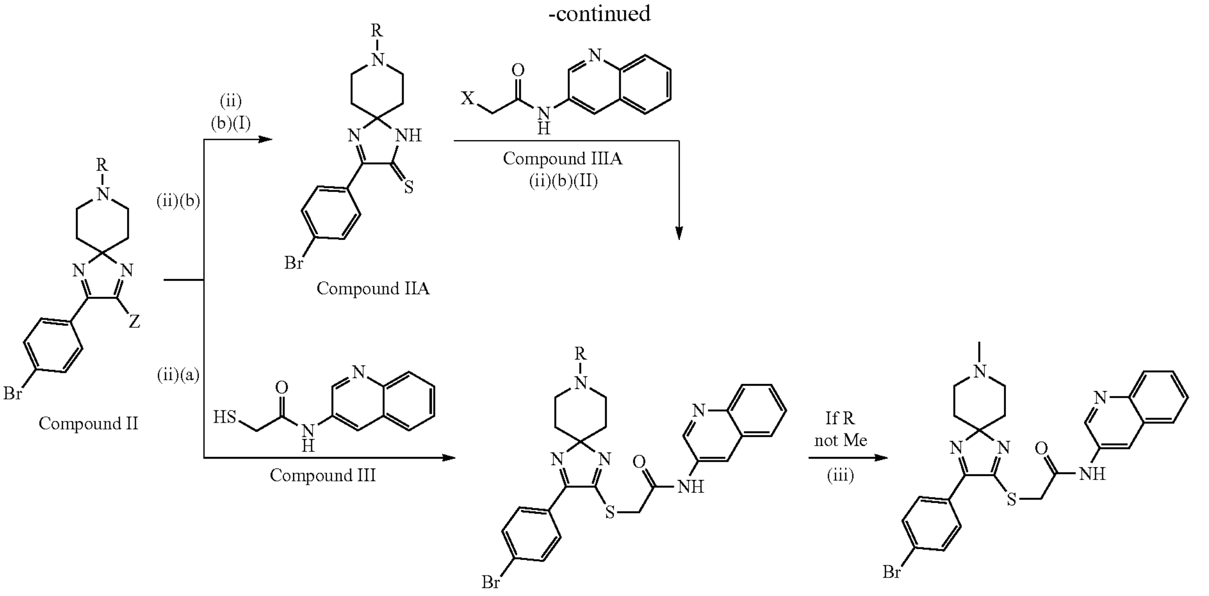

Compound II

Compound IIA

Compound IIIA

Compound III

Compound IV or
Compound A if R = Me

Compound A

Scheme 3 is not intended to be limiting in scope. For example, when necessary, step (iii) to remove a nitrogen-protecting group for R and replace it with a methyl group for R may precede or follow step (ii)(a) or (ii)(b). In some cases, step (iii) can take place between steps (ii)(b)(I) and (ii)(b)(II).

Synthesis of Compound II

The processes of the disclosure can include synthesizing Precursor V:

(Precursor V)

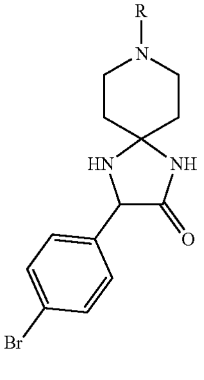

As used throughout, R is methyl or a nitrogen-protecting group. In some cases, R is a $CD_3$ group (i.e., a deuterated methyl group). Nitrogen-protecting groups are generally known in the art. Nonlimiting examples of nitrogen-protecting groups include carbobenzyloxy (Cbz) groups, acetyl groups, t-butyloxycarbonyl (Boc) groups, and 9-fluorenylmethyloxycarbonyl (Fmoc) groups.

In particular, an α-aminoamide (Precursor III) can be reacted with a piperidin-4-one (Precursor IV) to form a substituted 1,4,8-triazaspiro[4.5]decan-2-one (Precursor V):

(Precursor III)

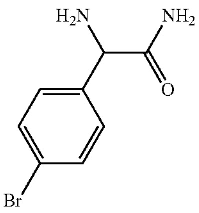

and (Precursor IV)

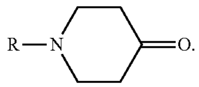

In some embodiments, the formation of Precursor V is carried out in an organic solvent. Organic solvents are generally known in the art. Nonlimiting examples of organic solvents that can be used throughout the processes described herein include ethyl acetate, acetonitrile, toluene, benzene, xylene, chlorobenzene, fluorobenzene, naphthalene, benzotrifluoride, tetrahydrofuran (THF), tetrahydropyran, dimethylformamide (DMF), tetrahydrofurfuryl alcohol, diethyl ether, dibutyl ether, diisopropyl ether, methyl tert-butyl ether (MTBE), 2-methyltetrahydrofuran (2-MeTHF), dimethyl sulfoxide (DMSO), 1,2-dimethoxyethane (1,2-DME), 1,2-dichloroethane (1,2-DCE), 1,4-dioxane, cyclopentylmethyl ether (CPME), chloroform, carbon tetrachloride, dichloromethane (DCM), 2-butanone, methanol, ethanol, propanol, and 2-propanol, or a combination thereof. In some embodiments, the formation of Precursor V is carried out in ethanol. In some embodiments, the formation of Precursor V is carried out at elevated temperature. In some embodiments, the formation of Precursor V is carried out at a temperature of 20° C. to 100° C., for example, at least 20, 30, 40, 50, 60, 70, 80, or 100° C. and/or up to 60, 70, 80, 90, or 100° C., such as 20° C. to 80° C., 40° C. to 80° C., to 90° C., 60° C. to 80° C., 75° C. to 85° C., or 70° C. to 80° C. In some embodiments, the formation of Precursor V occurs at a temperature of 80° C.

The processes of the disclosure can include synthesizing Compound I.

(I)

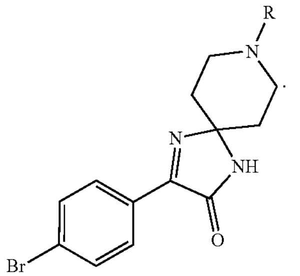

In particular, Precursor V can be oxidized to form Compound I. In some embodiments, Compound I is formed via an addition-elimination reaction. In some embodiments, Compound I is formed by treating Precursor V with 2,3-dichloro-5,6-dicyano-1,4-benzoquinone (DDQ). In some embodiments, Compound I is formed by treating Precursor V with an α-bromination reagent, followed by elimination of an equivalent of HBr. In some embodiments, Compound I is formed by treating Precursor V with N-bromosuccinimide (NBS), followed by heating to form Compound I. In some embodiments, Compound I is formed by treating Precursor V with NBS in the presence of UV light to form Compound I. In some embodiments, Compound I is formed by treating Precursor V with NBS in the presence of UV light and with heating to form Compound I. In some embodiments, the UV light has a wavelength of 365 nm. In some embodiments, Compound I is formed by treating Precursor V with NBS in an organic solvent. In some embodiments, Compound I is formed by treating Precursor V with NBS in DCM. In some embodiments, Compound I is formed in the presence of a base. Non-limiting examples of bases include alkylamines, such as mono-, di, or trialkylamines (e.g., monoethylamine, diethylamine, triethylamine, and N,N-diisopropylethylamine (DIPEA)), pyridines, such as collidine and 4-dimethylaminopyridine (DMAP), and imidazoles, such as N-methylimidazole, as well as benzylamine, methylbenzylamine, morpholine, piperidine, picoline, dicyclohexylamine, N,N'-dibenzylethylenediamine, 2-hydroxyethylamine, bis-(2-hydroxyethy)amine, tri-(2-hydroxyethyl)amine, procaine, dibenzylpiperidine, dehydroabietylamine, N,N'-bisdehydroabietylamine, glucamine, N-methylglucamine, quinine, quinoline, lysine, arginine, 1,4-diazabicyclo[2.2.2]octane (DABCO), lutidine, poly(4-vinylpyridine), $Na_2CO_3$, $K_2CO_3$, $Cs_2CO_3$, $CaCO_3$, LiH, NaH, KH, NaOH, LiOH, and KOH. In some cases, the base is a trialkylamine (e.g., triethylamine or N,N-diisopropylethylamine (DIPEA)), lutidine, collidine, $Na_2CO_3$, $K_2CO_3$, $Cs_2CO_3$, $CaCO_3$, LiH, NaH, or KH. In some embodiments, the formation of Compound I is carried out at elevated temperature. In some embodiments, the formation of Compound I is carried out at a temperature of 20° C. to 50° C., for example, at least 20, 25, 30, 35, 40, 45, or 50° C. and/or up to 20, 25, 30, 35, 40, 45, or 50° C., such as 20° C. to 50° C., 30° C. to 50° C., 40° C. to 50° C., or 30° C. to 40° C. In some embodiments, the formation of Compound I occurs at a temperature of 35° C. to 45° C. or 35° C. to 40° C. In some embodiments, the formation of Compound I occurs at a temperature of about 40° C.

The processes of the disclosure can include synthesizing Compound II:

(II)

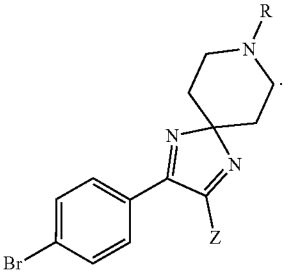

As used throughout, Z is a halogen or a sulfonate group. In some cases, Z is chloride. In some cases, Z is triflate.

In particular, Compound I can be admixed with a halogenation reagent or a sulfonylation reagent to form Compound II. Halogenation reagents and sulfonylation reagents are generally known in the art. In some cases, the halogenation reagent is a chlorination reagent. Nonlimiting examples of chlorination reagents that can be used throughout the processes described herein include $SOCl_2$, $POCl_3$, Vilsmeier reagents, oxalyl chloride, $PCl_5$, $SOBr_2$, and $POBr_3$. Nonlimiting examples of sulfonylation reagents that can be used throughout the processes described herein include triflic anhydride, mesyl chloride, mesic anhydride, tosyl chloride, tosic anhydride, benzenesulfonyl chloride, benzenesulfonic anhydride, nosyl chloride, and perfluoroalkylsulfonic anhydrides. In some embodiments, Compound I is admixed with a halogenation reagent to form Compound II. In some embodiments, Compound I is admixed with a chlorination reagent to form Compound II. In some embodiments, Compound I is admixed with a sulfonylation reagent to form Compound II. In some embodiments, Compound I is admixed with triflic anhydride to form Compound II.

In some embodiments, Compound II is formed by admixing Compound I with a halogenation or sulfonylation reagent in an organic solvent. In some embodiments, Compound II is formed by admixing Compound I with a halogenation or sulfonylation reagent in DCM. In some embodiments, Compound II is formed by admixing Compound I with a halogenation or sulfonylation reagent in ethyl acetate. In some embodiments, Compound II is formed by admixing Compound I with a halogenation or sulfonylation reagent in a mixture of organic solvents. In some embodiments, Compound II is formed by admixing Compound I with a halogenation or sulfonylation reagent in a mixture of DCM and ethyl acetate. In some embodiments, Compound II is formed by admixing Compound I with a chlorination or sulfonylation reagent in an organic solvent. In some embodiments, Compound II is formed by admixing Compound I with a chlorination or sulfonylation reagent in a mixture of organic solvents. In some embodiments, Compound II is formed by admixing Compound I with a chlorination or sulfonylation reagent in a mixture of DCM and ethyl acetate. In some embodiments, DCM and ethyl acetate are present in a volume ratio of 2:1, 1.9:1, 1.8:1, 1.7:1, 1.6:1, 1.5:1, 1.4:1, 1.3:1, 1.2:1, 1.1:1, or 1:1. In some embodiments, DCM and ethyl acetate are present in a volume ratio of 1.5:1.

In some embodiments, Compound II is formed by admixing Compound I with a chlorination or sulfonylation reagent in a mixture of DCM and ethyl acetate in the presence of a base. Non-limiting examples of bases include alkylamines, such as trialkylamines (e.g., triethylamine, or N,N-diisopropylethylamine (DIPEA)), pyridines, such as collidine and 4-diethylaminopyridine (DMAP), and imidazoles, such as N-methylimidazole, as well as dimethylbenzylamine, N-methylmorpholine, N-methylpiperidine, picoline, N-methyldicyclohexylamine, N,N'-dibenzylethylenediamine, tri-(2-hydroxyethyl)amine, procaine, dibenzylpiperidine, dehydroabietylamine, N,N'-bisdehydroabietylamine, N-methylglucamine, quinine, quinoline, lysine, arginine, 1,4-diazabicyclo[2.2.2]octane (DABCO), N,N-diisopropylethylamine, lutidine, poly(4-vinylpyridine), $Na_2CO_3$, $K_2CO_3$, $Cs_2CO_3$, LiH, NaH, KH, NaOH, LiOH, and KOH. In some cases, the base is a trialkylamine (e.g., triethylamine or N,N-diisopropylethylamine (DIPEA)), lutidine, collidine, $Na_2CO_3$, $K_2CO_3$, $Cs_2CO_3$, $CaCO_3$, LiH, NaH, or KH. In some cases, the base is a trialkyl amine, or more specifically, comprises triethylamine or DIPEA. In some embodiments, Compound II is formed by admixing Compound I with a chlorination or sulfonylation reagent in a mixture of DCM and ethyl acetate in the presence of DIPEA. In some embodiments, the base and Compound I are present in a molar ratio of 2:1, 1.9:1, 1.8:1, 1.7:1, 1.6:1, 1.5:1, 1.4:1, 1.3:1, 1.2:1, 1.1:1, or 1:1. In some embodiments, the base and Compound I are present in a molar ratio of 1.5:1. In some embodiments, DIPEA and Compound I are present in a molar ratio of 1.5:1.

In some embodiments, Compound II is formed by admixing Compound I with a chlorination or sulfonylation reagent in the presence of di-tert-butyl dicarbonate ($Boc_2O$), and optionally a base as described above. In some embodiments, Compound II is formed by admixing Compound I with a chlorination or sulfonylation reagent in a mixture of DCM and ethyl acetate in the presence of DIPEA and $Boc_2O$. In some embodiments, $Boc_2O$ and Compound I are present in a molar ratio of 2:1, 1.9:1, 1.8:1, 1.7:1, 1.6:1, 1.5:1, 1.4:1, 1.3:1, 1.2:1, 1.1:1, or 1:1. In some embodiments, $Boc_2O$ and Compound I are present in a molar ratio of 1:1.

In some embodiments, the formation of Compound II is carried out at elevated temperature. In some embodiments, the formation of Compound II is carried out at a temperature of 20° C. to 50° C., for example, at least 20, 25, 30, 35, 40, 45, or 50° C. and/or up to 20, 25, 30, 35, 40, 45, or 50° C., such as 20° C. to 50° C., 30° C. to 50° C., 40° C. to 50° C., or 30° C. to 40° C. In some embodiments, the formation of Compound II occurs at a temperature of 35° C. to 40° C. In some embodiments, the formation of Compound II occurs at a temperature of 40° C.

In some embodiments, Compound I and/or Compound II is present as a salt. A salt of Compound I, Compound II, or any other compound described herein (e.g., Compound A) can be prepared, for example, by reacting the compound in its free form with a suitable organic or inorganic acid, and optionally isolating the salt thus formed. Nonlimiting examples of suitable acid salts include hydrobromide, hydrochloride, sulfate, bisulfate, sulfonate, camphorsulfonate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulfonate salts, and amino acid salts.

Synthesis of Compound A Via Step (ii)(a)

The processes of the disclosure can include synthesizing Compound A via reaction of Compound II and Compound III (via step (ii)(a)) when R is methyl. The same process synthesizes Compound IV when R is a nitrogen-protecting group. In particular, the processes of the disclosure can include admixing Compound II and Compound III in the presence of a base to form Compound A either directly or indirectly via Compound IV:

(III)

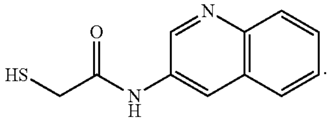

In some embodiments, the base is LiH, NaH, KH, LDA, KHMDS, NaHMDS, LiHMDS, $Na_2CO_3$, $K_2CO_3$, $Cs_2CO_3$, NaOH, LiOH, KOH, sodium methoxide, sodium ethoxide, sodium tert-butoxide or potassium tert-butoxide. In some embodiments, the base is NaH. In some embodiments, the base and Compound III are present in a molar ratio of 2:1, 1.9:1, 1.8:1, 1.7:1, 1.6:1, 1.5:1, 1.4:1, 1.3:1, 1.2:1, 1.1:1, or 1:1. In some embodiments, the base and Compound III are present in a molar ratio of 1:1.

In some embodiments, Compound II and Compound III are present in a molar ratio of 2:1, 1.9:1, 1.8:1, 1.7:1, 1.6:1, 1.5:1, 1.4:1, 1.3:1, 1.2:1, 1.1:1, or 1:1. In some embodiments, Compound II and Compound III are present in a molar ratio of 1:1.

In some embodiments, Compound A is formed by admixing Compound II, Compound III, and a base in an organic solvent. In some embodiments, the organic solvent is ethyl acetate, dichloromethane (DCM), acetonitrile, tetrahydrofuran (THF), tetrahydropyran, dimethylformamide (DMF), diethyl ether, dibutyl ether, diisopropyl ether, methyl tert-butyl ether (MTBE), 2-methyltetrahydrofuran (2-MeTHF), dimethyl sulfoxide (DMSO), 1,2-dimethoxyethane (1,2-DME), or 1,4-dioxane, or a combination thereof.

Synthesis of Compound A Via Step (ii)(b)

The processes of the disclosure can include synthesizing Compound A via formation of Compound IIA then reaction with Compound IIIA (step (ii)(b)) when R is methyl. The same process synthesizes Compound IV when R is a nitrogen-protecting group. In particular, the processes of the disclosure can include admixing Compound II and a nucleophilic sulfuration reagent source to form Compound IIA then admixing Compound IIA with Compound IIIA in the presence of a base to form Compound A either directly or indirectly via Compound IV:

(IIA)

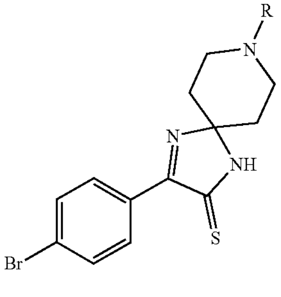

and (IIIA)

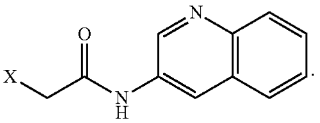

The processes of the disclosure can include synthesizing Compound IIA:

(IIA)

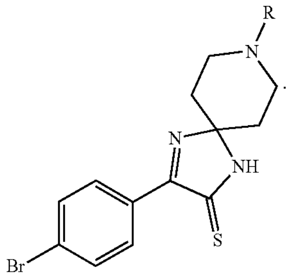

In particular, Compound II can be admixed with a nucleophilic sulfuration reagent to form Compound IIA. Non-limiting examples of nucleophilic sulfuration reagents include $Li_2S$, $Na_2S$, $K_2S$, NaSH, AcSK, thiourea, $Li_2S_x$, $Na_2S_x$, $K_2S_x$, (wherein x=2–) and $NaBH_4/S$. In some embodiments, Compound IIA is formed by treating Compound II with $Na_2S$. In some embodiments, Compound IIA is formed by treating Compound II with a hydrate of $Na_2S$. In some embodiments, Compound IIA is formed by treating Compound II with $Na_2S \cdot 4H_2O$. In some embodiments, admixing Compound II and a nucleophilic sulfuration reagent occurs in the presence of a phase transfer catalyst. Non-limiting examples of phase transfer catalysts include tetrabutylammonium chloride (TBACI), tetrabutylammonium bromide (TBAB), and tetrabutylammonium iodide (TBAI). In some embodiments, the nucleophilic sulfuration reagent and Compound II are present in a molar ratio of 2:1, 1.9:1, 1.8:1, 1.7:1, 1.6:1, 1.5:1, 1.4:1, 1.3:1, 1.2:1, 1.1:1, or 1:1. In some embodiments, the nucleophilic sulfuration reagent and Compound II are present in a molar ratio of 1.5:1. In some embodiments, Compound IIA is formed by admixing the nucleophilic sulfuration reagent and Compound II in a mixture of organic solvents. In some embodiments, Compound IIA is formed by admixing the nucleophilic sulfuration reagent and Compound II in a mixture of DCM and ethyl acetate. In some embodiments, DCM and ethyl acetate are present in a volume ratio of 2:1, 1.9:1, 1.8:1, 1.7:1, 1.6:1, 1.5:1, 1.4:1, 1.3:1, 1.2:1, 1.1:1, or 1:1. In some embodiments, DCM and ethyl acetate are present in a volume ratio of 1.5:1.

The processes of the disclosure can include synthesizing Compound A via step (ii)(b). In particular, the processes of the disclosure can include admixing Compound IIA and Compound IIIA to form Compound A:

(IIIA)

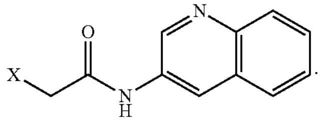

As used throughout, X is halogen. In some embodiments, X is I, Br, or Cl. In some embodiments, X is Br or CI In some embodiments, X is Cl.

In particular, Compound IIA can be admixed with Compound IIIA to form Compound A.

In some embodiments, Compound A is formed by admixing Compound IIA and Compound IIIA in the presence of a base. In some embodiments, the base is NaH, $Na_2CO_3$, $K_2CO_3$, $Cs_2CO_3$, NaOH, LiOH, or KOH, or a combination thereof. In some embodiments, the base comprises $K_2CO_3$. In some embodiments, the base is a trialkylamine, pyridine, a pyridine derivative, or combinations thereof. In some embodiments, the base is a trialkylamine. In some embodiments, the trialkylamine is triethylamine or DIPEA. In some embodiments, the base and Compound IIA are present in a molar ratio of 5:1, 4:1, 3:1, 2:1, or 1:1. In some embodiments, the base and Compound IIA are present in a molar ratio of 2:1.

In some embodiments, Compound IIA, Compound IIIA, and a base are admixed in an organic solvent. In some embodiments, the organic solvent is ethyl acetate, dichloromethane (DCM), 2-butanone, acetonitrile, tetrahydrofuran (THF), tetrahydropyran, dimethylformamide (DMF), tetrahydrofurfuryl alcohol, diethyl ether, dibutyl ether, diisopropyl ether, methyl tert-butyl ether (MTBE), 2-methyltetrahydrofuran (2-MeTHF), dimethyl sulfoxide (DMSO), 1,2-dimethoxyethane (1,2-DME), 1,4-dioxane, methanol, ethanol, propanol, or 2-propanol, or a combination thereof. In some embodiments, the organic solvent comprises 2-propanol.

In some embodiments, admixing Compound IIA, Compound IIIA, and the base is carried out at elevated temperature. In some embodiments, the temperature is 20° C. to 50° C., for example, at least 20, 25, 30, 35, 40, 45, or 50° C. and/or up to 20, 25, 30, 35, 40, 45, or 50° C., such as 20° C. to 50° C., 30° C. to 50° C., 40° C. to 50° C., or 30° C. to 40° C. In some embodiments, the temperature is 40° C. to 45° C. In some embodiments, the temperature is 45° C.

Synthesis of Compound A Via Step (iii)

The processes of the disclosure can include removing the nitrogen protecting group of R and methylating the intermediate amine to form Compound A where R is methyl (e.g., via step (iii)) or form a compound intermediate where R is methyl (Compound II or Compound IIA). This modification of R from nitrogen protecting group to methyl group can occur for Compound II, Compound IIA, or Compound IV, e.g., can occur before or after any step of the disclosed processes. In some cases, the processes disclosed comprise converting Compound IV to Compound A.

Removal of the nitrogen-protecting group can comprise admixing the compound (e.g., Compound II, Compound IIA, or Compound IV) in the presence of acid. Nonlimiting examples of suitable acids include hydrobromic, hydrochloric, sulfuric, sulfonic, phosphoric, nitric, acetic, trifluoroacetic, benzoic, and tosic acid. In some embodiments, the acid comprises hydrochloric acid. In some embodiments, the acid and compound (Compound II, Compound IIA, or Compound IV) are present in a molar ratio of 20:1, 15:1, 12:1, 11:1, 10:1, 9:1, 8:1, 7:1, 6:1, 5:1, 4:1, 3:1, 2:1, or 1:1. In some embodiments, the acid and compound (Compound II, Compound IIA, or Compound IV) are present in a molar ratio of 10:1.

In some embodiments, removal of the nitrogen protecting group can occur in the presence of an acid and an organic solvent. In some embodiments, the organic solvent is dichloromethane (DCM), chloroform, 1,2-dichloroethane, ethyl acetate, acetonitrile, tetrahydrofuran (THF), tetrahydropyran, dimethylformamide (DMF), tetrahydrofurfuryl alcohol, diethyl ether, dibutyl ether, diisopropyl ether, methyl tert-butyl ether (MTBE), 2-methyltetrahydrofuran (2-MeTHF), dimethyl sulfoxide (DMSO), 1,2-dimethoxyethane (1,2-DME), 1,4-dioxane, methanol, ethanol, propanol, or 2-propanol, or a combination thereof. In some embodiments, the organic solvent comprises methanol.

Removal of the nitrogen-protecting group can comprise catalytic hydrogenation of the compound (e.g., Compound II, Compound IIA, or Compound IV). Non-limiting examples of suitable hydrogenation catalysts include nickel catalysts (e.g., $Ni/Al_2O_3$), palladium catalysts (e.g., Pd/C) and platinum catalysts (e.g., Pt/C). In some embodiments, the hydrogenation catalyst is Pd/C.

In some embodiments, removal of the nitrogen protecting group can occur in the presence of hydrogen gas, a hydrogenation catalysts, and an organic solvent. In some embodiments, the organic solvent is dichloromethane (DCM), chloroform, 1,2-dichloroethane, tetrahydrofuran (THF), tetrahydropyran, tetrahydrofurfuryl alcohol, diethyl ether, dibutyl ether, diisopropyl ether, methyl tert-butyl ether (MTBE), 2-methyltetrahydrofuran (2-MeTHF), 1,2-dimethoxyethane (1,2-DME), 1,4-dioxane, methanol, ethanol, propanol, or 2-propanol, or a combination thereof. In some embodiments, the organic solvent comprises methanol.

In some embodiments, removal of the nitrogen protecting group is carried out at ambient temperature. In some embodiments, the temperature can be 20° C. to 30° C., for example, at least 20, 25, or 30° C. and/or up to 20, 25, or 30° C., such as 20° C., 21° C., 22° C., 23° C., 24° C., 25° C., 26° C., 27° C., 28° C., 29° C., or 30° C. In some embodiments, the temperature is 20° C. to 25° C. In some embodiments, the temperature is 25° C.

Methylation of the deprotected amine can be performed by admixing the deprotected amine with a methylating agent. In some embodiments, the processes comprise admixing the deprotected amine compound derived from Compound II, Compound IIA, or Compound IV with a methylating agent, and a base if required. Nonlimiting examples of suitable methylating agents include methyl iodide, dimethyl sulfate, methyl tosylate, methyl bromide, all in the presence of a suitable base, a combination of $NaBH_3CN$, $CH_2O$, and acetic acid, a combination of $NaBH_4$, $CH_2O$, and acetic acid, a combination of $NaBH(OAc)_3$, $CH_2O$, $Et_3N$, a combination of $NaBH(OAc)_3$, $CH_2O$, and acetic acid, or $CH_2O$ and $H_2$ in presence of Ni, Pt, or Pd catalysts. In some embodiments, the methylating agent is a combination of $NaBH(OAc)_3$, $CH_2O$, and acetic acid. In some embodiments, the combination of $NaBH(OAc)_3$, $CH_2O$, and acetic acid is present in a molar ratio of 3:2:3 $NaBH(OAc)_3$:$CH_2O$:acetic acid per mole of deprotected amine derived from Compound II, Compound IIA, or Compound IV.

In some embodiments, the methylation is carried out at low temperature (e.g., a temperature below room temperature, 25° C.). In some embodiments, the temperature is 0° C. to 20° C., for example, at least 0, 5, 10, 15, or 20° C. and/or up to 0, 5, or 10° C., such as 0° C., 1° C., 2° C., 3° C., 4° C., 5° C., 6° C., 7° C., 8° C., 9° C., or 10° C. In some embodiments, the temperature is 0° C. to 5° C. In some embodiments, the temperature is 5° C.

It is to be understood that while the disclosure is read in conjunction with the detailed description thereof, the foregoing description and following example are intended to illustrate and not limit the scope of the disclosure, which is defined by the scope of the appended claims. Other aspects, advantages, and modifications are within the scope of the appended claims.

EXAMPLES

The following examples are provided for illustration and are not intended to limit the scope of the disclosure.

Example 1: Synthesis of Compound II

Precursor III (2-amino-2-(4-bromophenyl)acetamide) was prepared according to the following reaction scheme:

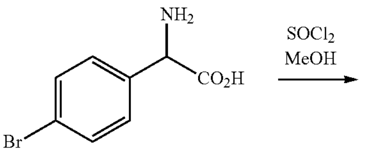

Precursor I

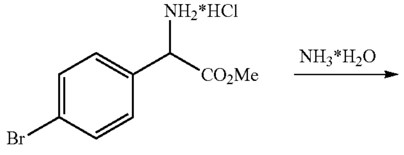

Precursor II

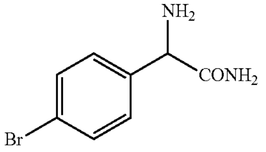

Precursor III

Precursor I (2-amino-2-(4-bromophenyl)acetic acid, 1.75 kg, 7.6 mol, 1.0 eq.) was charged into a 30 L reactor with methanol (12.3 L, 7 volumes) under nitrogen atmosphere. The nitrogen was purged three times, and the reaction mixture was cooled to 0° C. To this solution was added $SOCl_2$ (1.36 kg, 11.4 mol, 1.5 eq.) dropwise to the solution at 10-20° C. The reaction was stirred at 10-20° C. for 0.5 h, then warmed to 30-35° C. and stirred for 6 h. The solution was partially concentrated under reduced pressure to 5 L at 40° C., MTBE was added (18 L, 10 v), and the mixture was stirred for 1 h at 5-10° C. The solution was filtered, and the filter cake was washed with MTBE (3 L, 2 v). The filter cake was dried under reduced pressure at 40° C. to obtain Precursor II with 98 A % purity in an 82% yield.

Precursor II (1.75 kg, 6.2 mol, 1.0 eq.) was charged into a 20 L reactor with $NH_3 \cdot H_2O$ (28%, 8.8 L, 5 v). The mixture was stirred at 10-15° C. for 20 h, then filtered and the filter cake washed with water (3.5 L, 2 v). The filter cake was dried under reduced pressure at 50° C. to obtain Precursor III (2-amino-2-(4-bromophenyl)acetamide) with 96 A % purity in an 85% isolated yield.

Precursor V (tert-butyl 2-(4-bromophenyl)-3-oxo-1,4,8-triazaspiro[4.5]decane-8-carboxylate) was prepared according to the following reaction scheme:

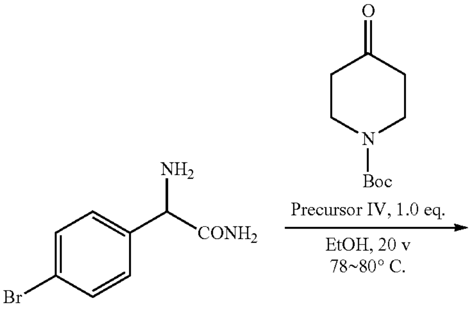

Precursor III

-continued

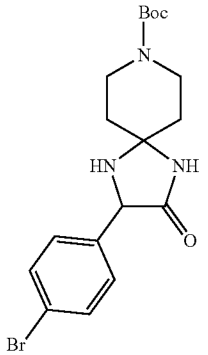

Precursor V

Precursor III (2-amino-2-(4-bromophenyl)acetamide, 500.0 g, 2.18 mol, 1.0 eq), Precursor IV (436.7 g, 2.18 mol, 1.0 eq.), and EtOH (10 L, 20 v) were charged into a 20 L reactor. The reaction reactor was purged with $N_2$ three times, and then the reaction mixture was heated to reflux and stirred for 16 h. The mixture was concentrated to ca. 2 v under reduced pressure at 45° C., and then water (7 L, 7 v) was added and stirred at 15-20° C. for 0.5 h. The reaction mixture was filtered and the filter cake was washed with 2:7 EtOH/water (v/v, 1 L, 1 vol). The filter cake was dried under reduced pressure at 50° C. to give Precursor V (tert-butyl 2-(4-bromophenyl)-3-oxo-1,4,8-triazaspiro[4.5]decane-8-carboxylate) with 98% LC purity in a 76% isolated yield.

Compound I (tert-butyl 2-(4-bromophenyl)-3-oxo-1,4,8-triazaspiro[4.5]dec-1-ene-8-carboxylate) was synthesized according to the following reaction scheme:

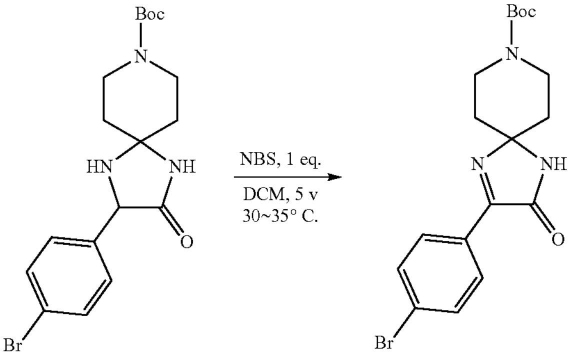

Precursor V Compound I

Precursor V (tert-butyl 2-(4-bromophenyl)-3-oxo-1,4,8-triazaspiro[4.5]decane-8-carboxylate, 1.5 kg, 1.0 eq.), $Na_2CO_3$ (194 g, 0.5 eq.) and DCM (15 L, 10 v) were charged into a 30 L reactor, which was purged with $N_2$ three times and cooled to 0° C. NBS (651.4 g, 1.0 eq.) was charged in four portions into the mixture. The reaction was stirred at 30-35° C. for 20 h. The reaction mixture was irradiated with UV light at 365 nm for 1 h, then stirred at 30-35° C. for 4 h. To this mixture was added 20 wt % aq. $Na_2CO_3$ (7.5 L, 5 v) and $(Boc)_2O$ (80 g, 0.1 eq.) and the mixture was stirred for 30 min.

The reaction mixture was worked up as follows: The aqueous phase was separated and extracted with DCM (15 L×2, 10 v×2). The organic phase was concentrated to dryness under reduced pressure at 35-40° C. The product was slurried in EtOH (4.5 L, 3 v), the mixture was filtered, and the filter cake was dried under reduced pressure at 35-40° C. to give Compound I (tert-butyl 2-(4-bromophenyl)-3-oxo-1,4,8-triazaspiro[4.5]dec-1-ene-8-carboxylate) with 96.4% HPLC purity in an 81% isolated yield.

Compound II (tert-butyl 2-(4-bromophenyl)-3-(((trifluoromethyl)sulfonyl)oxy)-1,4,8-triazaspiro[4.5]deca-1,3-diene-8-carboxylate) was synthesized according to the following reaction scheme:

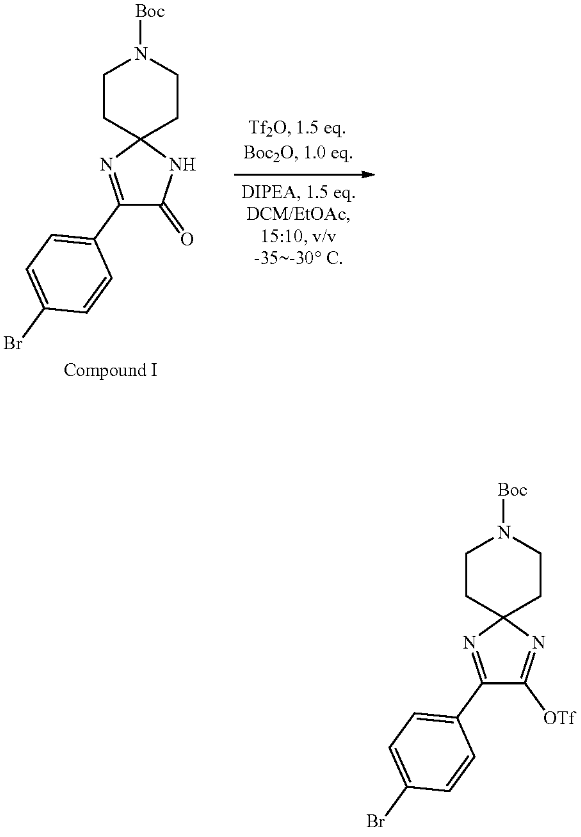

Compound I

Compound II

Compound I (tert-butyl 2-(4-bromophenyl)-3-oxo-1,4,8-triazaspiro[4.5]dec-1-ene-8-carboxylate, (600 g, 1.0 eq.), $Boc_2O$ (320.8 g, 1.0 eq.), DCM (9.0 L, 15 v) and EtOAc (6.0 L, 10 v) were charged into a reactor under $N_2$. To this mixture was added DIPEA (284.3 g, 1.5 eq.). The mixture was purged with $N_2$ three times, the solution was cooled to −30° C., and a solution of $Tf_2O$ (620.7 g, 1.5 eq.) in DCM (1.2 L, 2 v) was added into the mixture at −30° C. The mixture was stirred at −30° C. for 1 h to produce Compound II (tert-butyl 2-(4-bromophenyl)-3-(((trifluoromethyl)sulfonyl)oxy)-1,4,8-triazaspiro[4.5]deca-1,3-diene-8-carboxylate) in 90.2 A % purity, the solution of which was directly used in the next step.

Example 2: Synthesis of Compound A Via Steps (ii)(b) and (iii)

Compound IIA (tert-butyl 2-(4-bromophenyl)-3-thioxo-1,4,8-triazaspiro[4.5]dec-1-ene-8-carboxylate) was synthesized according to the following reaction scheme:

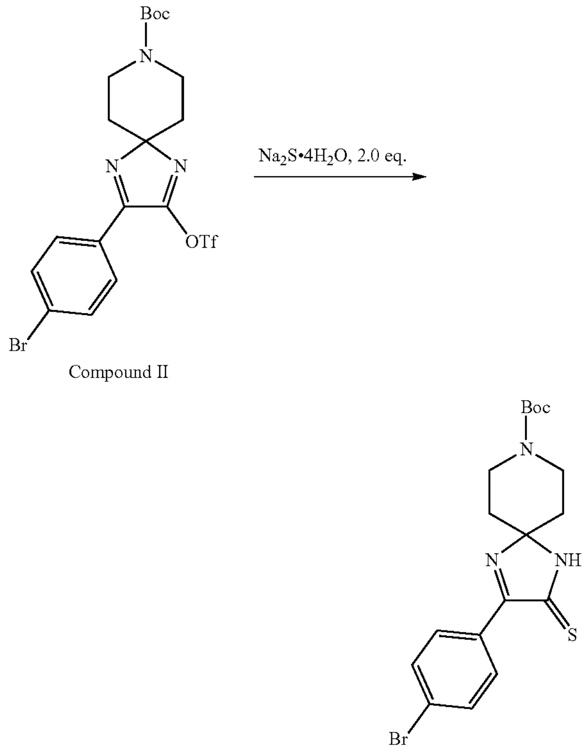

Compound II

Compound IIA

To a solution of Compound II (tert-butyl 2-(4-bromophenyl)-3-oxo-1,4,8-triazaspiro[4.5]dec-1-ene-8-carboxylate, in DCM (9.0 L, 15 v) and EtOAc (6.0 L, 10 v) under $N_2$ as prepared in Example 1 was added neat $Na_2S \cdot 4H_2O$ (461.0 g, 2.0 eq.) and stirred at −30° C. for 1 h. To this solution was added water (10 L, 10 v) followed by EtOAc (10 L, 10 v) at −30 to −10° C. This mixture was stirred for 0.5 h at −10 to 0° C. The mixture was filtered and dried under reduced pressure at 40° C. giving Compound IIA (tert-butyl 2-(4-bromophenyl)-3-thioxo-1,4,8-triazaspiro[4.5]dec-1-ene-8-carboxylate) in 98% HPLC purity in an 82% corrected yield.

The methylated derivative of Compound IIA ("Compound IIA-Me", 3-(4-bromophenyl)-8-methyl-1,4,8-triazaspiro[4.5]dec-3-ene-2-thione) was synthesized according to the following reaction scheme:

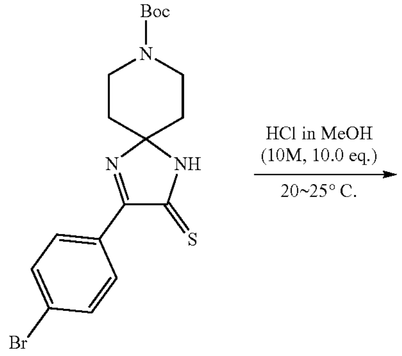

Compound IIA

-continued

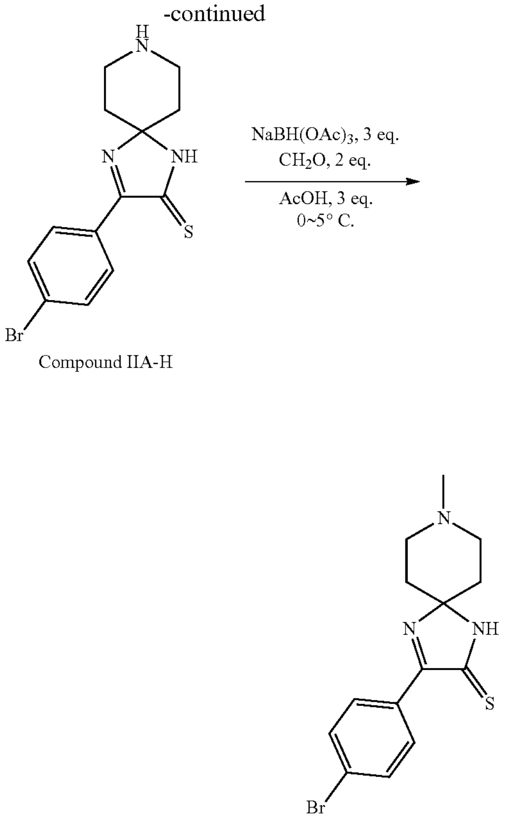

Compound IIA-H

Compound IIA-Me

Under $N_2$, Compound IIA (tert-butyl 2-(4-bromophenyl)-3-thioxo-1,4,8-triazaspiro[4.5]dec-1-ene-8-carboxylate, 530 g, 1.0 eq.) and DCM (26.5 L, 50 v) were charged into a 30 L reactor. The solution was cooled to 0° C., and HCl in MeOH (10 M, 1.25 L, 10.0 eq.) was added. The solution was warmed to 20-25° C. and stirred for 3 h. The mixture was filtered, and the filter cake was washed with DCM, then dried under reduced pressure at 40° C. for 6 h to afford Compound IIA-H, 3-(4-bromophenyl)-1,4,8-triazaspiro[4.5]dec-3-ene-2-thione as its hydrochloride salt with 98.1% HPLC purity in a 90% isolated yield.

Under $N_2$, Compound IIA-H, (3-(4-bromophenyl)-1,4,8-triazaspiro[4.5]dec-3-ene-2-thione hydrochloride 630 g, 1.0 eq.), $CH_2O$ (283.5 g, 2.0 eq., 37 wt %), AcOH (315 g, 3.0 eq) and THF (9.5 L, 15 v) were charged into a 20 L reactor. The solution was purged with $N_2$ three times, and then cooled to 0° C. To this solution was added $NaBH(OAc)_3$ (1107 g, 3.0 eq) in 4 portions at 0 to 5° C. over 1 h. The solution was purged with $N_2$ three times and stirred at 0° C. for 1.5 h. To the solution was added sat. aq. $Na_2CO_3$ (15 L, 25 v) and then EtOAc (6.3 L, 10 v). This mixture was separated, and the organic phase was washed twice with sat. aq. $Na_2CO_3$ (6.3 L×2, 10 v×2), and then twice with brine (6.3 L×2, 10 v×2). The combined organic layers were combined and concentrated under reduced pressure at 40° C. to give Compound IIA-Me (3-(4-bromophenyl)-8-methyl-1,4,8-triazaspiro[4.5]dec-3-ene-2-thione) with 97.5% HPLC purity in an 86% isolated yield.

Compound A (2-((3-(4-bromophenyl)-8-methyl-1,4,8-triazaspiro[4.5]deca-1,3-dien-2-yl)thio)-N-(quinolin-3-yl)acetamide) was synthesized according to the following reaction scheme:

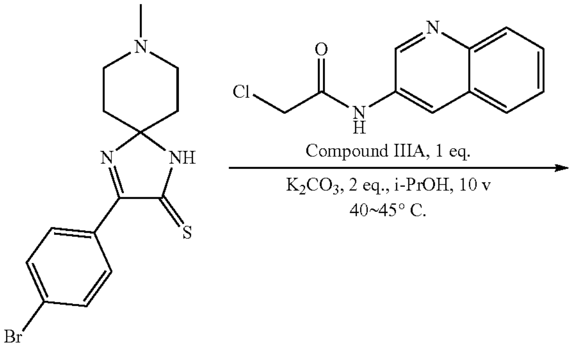

Compound IIA-Me

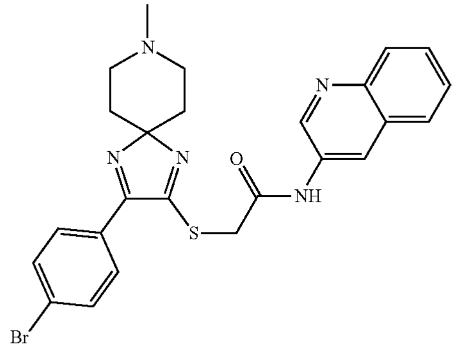

Compound A

Under an atmosphere of $N_2$, Compound IIA-Me (3-(4-bromophenyl)-8-methyl-1,4,8-triazaspiro[4.5]dec-3-ene-2-thione, 500 g, 1.0 eq.), Compound IIIA (325.2 g, 1.0 eq.) and i-PrOH (12.3 L, 15 v) were charged into a 30 L reactor and purged with $N_2$ three times. To this solution was added aq. $K_2CO_3$ (2 M, 1.48 L, 2.0 eq.), and the solution was stirred at 40° C. for 4 h. A THF solution of $Me_2NH$ (33 wt %, 1.00 kg) was added to the solution, and this mixture was stirred for 30 min. To this mixture was added water (2 L, 4 v), and the mixture was cooled to 10° C. and stirred for 1 h. The mixture was filtered and the filter cake washed with i-PrOH (500 mL, 1 v). The filter cake was dried under reduced pressure at 50° C. for 40 h to afford Compound A (2-((3-(4-bromophenyl)-8-methyl-1,4,8-triazaspiro[4.5]deca-1,3-dien-2-yl)thio)-N-(quinolin-3-yl)acetamide) with 99% LC purity in a 90% corrected (based on qNMR) yield.

Compound IIIA (2-chloro-N-(quinolin-3-yl)acetamide) was prepared as follows:

Quinolin-3-amine (285 g, 1.0 eq.), $Na_2CO_3$ (283 g, 1.0 eq.) and DCM (5.7 L, 20 v) were charged into a 10 L flask, which was purged with $N_2$ three times and cooled to −10° C. To this solution was added 2-chloroacetyl chloride (356 g, 1.5 eq.) at −10 to 0° C. over 0.5 h, and the solution was stirred at 20-25° C. for 1.5 h. The mixture was filtered and the filter cake was washed with DCM (300 mL, 1 v). The filter cake was dissolved in EtOAc (1.5 L, 5 v) and the solution was washed with aq. $Na_2CO_3$ (600 mL, 2 v). The organic phase was separated and washed with brine (1.5 L, 5 v×2), and then the organic phase was dried over $Na_2SO_4$ (600 g, 2 w). The solution was filtered, and the filter cake was washed with EtOAc (300 mL×2, 1 v×2). The filtrate was concentrated under reduced pressure at 45° C. to give Compound IIIA (2-chloro-N-(quinolin-3-yl)acetamide) with 98.3% LC purity in a 90% isolated yield.

Example 3: Alternate Synthesis of Compound A Via Steps (ii)(b) and (iii)

Compound I-Me (3-(4-bromophenyl)-8-methyl-1,4,8-triazaspiro[4.5]dec-3-en-2-one) was synthesized according to the following reaction scheme:

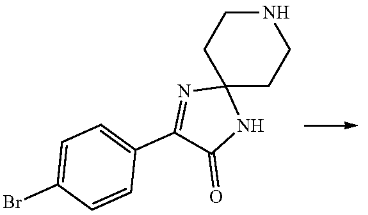

Compound I-H

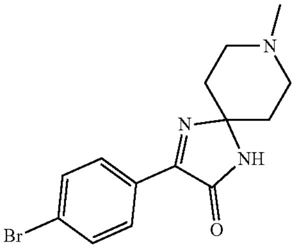

Compound I-Me

Compound I-H (3-(4-bromophenyl)-1,4,8-triazaspiro[4.5]dec-3-en-2-one) was synthesized as described in Example 5, below.

Compound I-H (3-(4-bromophenyl)-1,4,8-triazaspiro[4.5]dec-3-en-2-one, 1.0 g, 1.0 eq.), $CH_2O$ (1.3 g, 5.0 eq., 37 w %), AcOH (584 mg, 3.0 eq.) and THF (10 mL) were charged into a flask under $N_2$, and the flask was purged with $N_2$ three times. To this mixture was added $NaBH(OAc)_3$ (2.1 g, 3.0 eq.), the flask was purged with $N_2$ three times, and the solution was stirred at 20 to 25° C. for 1.5 h. To this mixture was added saturated aqueous $Na_2CO_3$ (10 mL), followed by EtOAc (10 mL). The organic phase was separated and washed twice with saturated aqueous $Na_2CO_3$ (10 mL×2), and then twice with brine (10 mL×2). The organic layer was concentrated under reduced pressure at 40° C. to give 750 mg of Compound I-Me 3-(4-bromophenyl)-8-methyl-1,4,8-triazaspiro[4.5]dec-3-en-2-one with 99% HPLC purity in a 72% isolated yield.

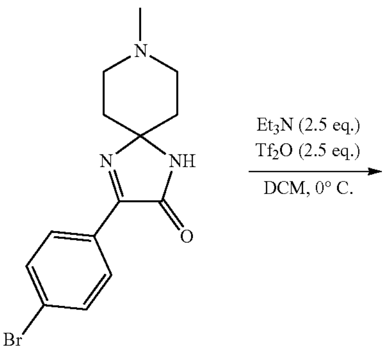

Compound I-Me

-continued

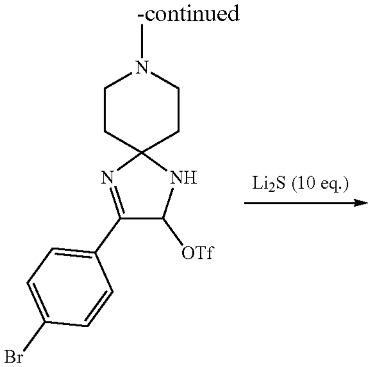

Compound II-Me

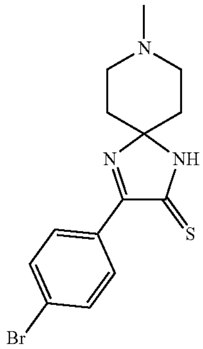

Compound IIA-Me

Under $N_2$, Compound I-Me (3-(4-bromophenyl)-8-methyl-1,4,8-triazaspiro[4.5]dec-3-en-2-one, 200 mg, 1.0 eq.) and DCM (2 mL) were charged into a flask, and to this mixture was added $Et_3N$ (157 mg, 2.5 eq.). The flask was purged with nitrogen three times, and the solution was cooled to −10° C. To this solution was added $Tf_2O$ (326 mg, 2.5 eq) in DCM (0.4 mL) to the solution, and the solution was further cooled to −15° C. The solution was stirred at −15° C. for 0.5 to afford Compound II-Me, 3-(4-bromophenyl)-8-methyl-1,4,8-triazaspiro[4.5]dec-3-en-2-yl trifluoromethanesulfonate.

To the solution of Compound II-Me, (3-(4-bromophenyl)-8-methyl-1,4,8-triazaspiro[4.5]dec-3-en-2-yl trifluoromethanesulfonate) was added $Li_2S$ (286 mg, 10.0 eq), and the mixture was stirred at −10° C. for 1 h. To the mixture was added water (2 mL) and then EtOAc (2 mL). The organic phase was separated and washed with water (2 mL) three times. The organic phase was concentrated to dryness under reduced pressure, and the product was slurried with EtOac (1 mL). The slurry was filtered and dried under reduced pressure at 40° C. to give Compound IIA-Me (3-(4-bromophenyl)-8-methyl-1,4,8-triazaspiro[4.5]dec-3-ene-2-thione) with 91% HPLC purity in a 36% corrected yield.

Compound A (2-((3-(4-bromophenyl)-8-methyl-1,4,8-triazaspiro[4.5]deca-1,3-dien-2-yl)thio)-N-(quinolin-3-yl)acetamide) was synthesized according to the following reaction scheme:

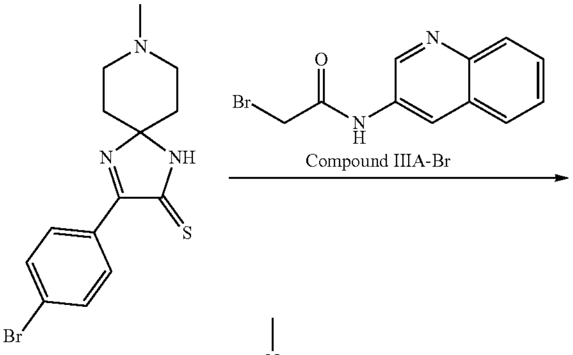

Compound IIA-Me

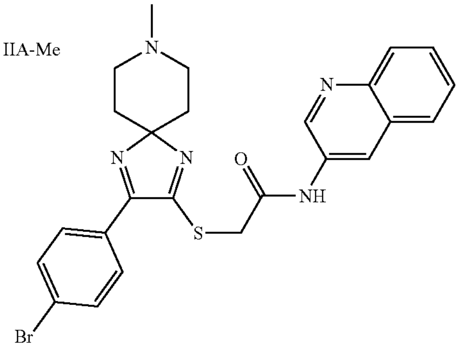

Compound A

Under an atmosphere of $N_2$, Compound IIA-Me (3-(4-bromophenyl)-8-methyl-1,4,8-triazaspiro[4.5]dec-3-ene-2-thione, 100 mg, 1.0 eq.) and DCM (1 mL) were charged into a flask and purged with $N_2$ three times. To this solution was added Compound IIIA-Br (78 mg, 1.0 eq) and DIPEA (77 mg, 2.0 eq), and the solution was stirred at 20° C. for 5 h. To this mixture was added water (1 mL) and DCM (1 mL), and the organic phase was separated and washed with water (1 mL) three times. The mixture was concentrated to dryness under reduced pressure at 40° C., and the mixture was purified by prep-TLC (eluting with 1:4 (v/v) DCM/MeOH) to afford 0.05 g of Compound A (2-((3-(4-bromophenyl)-8-methyl-1,4,8-triazaspiro[4.5]deca-1,3-dien-2-yl)thio)-N-(quinolin-3-Aacetamide) with 99% HPLC purity in a 32% corrected yield.

Example 4: Synthesis of Compound A-Boc Via Steps (ii)(b) and (iii)

Compound A-Boc (tert-butyl 2-(4-bromophenyl)-3-(2-oxo-2-(quinolin-3-ylamino)ethyl)thio)-1,4,8-triazaspiro[4.5]deca-1,3-diene-8-carboxylate) was synthesized according to the following reaction scheme:

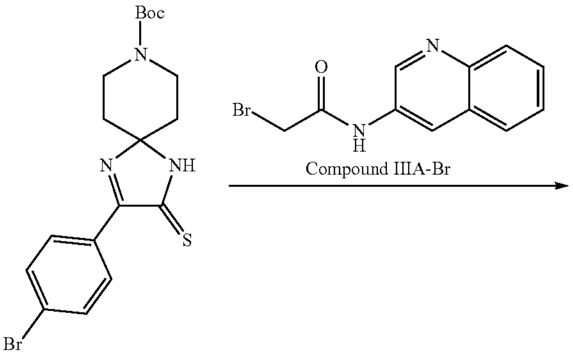

Compound IIA

-continued

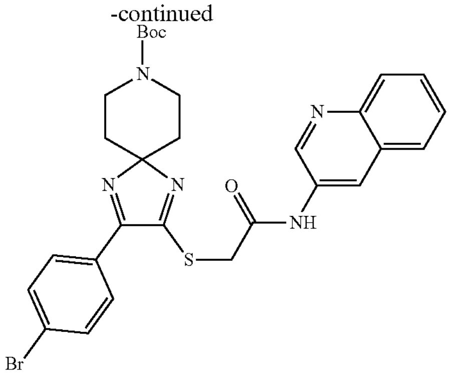

Compound A-Boc

Under an atmosphere of $N_2$, Compound IIA (tert-butyl 2-(4-bromophenyl)-3-thioxo-1,4,8-triazaspiro[4.5]dec-1-ene-8-carboxylate, 200 mg, 1.0 eq.) and DCM (2 mL) were charged into a flask and purged with $N_2$ three times. To this solution was added Compound IIIA-Br (150 mg, 1.2 eq) and $Et_3N$ (95 mg, 2.0 eq), and the solution was stirred at 20° C. for 1.5 h. To this mixture was added water (2 mL) and DCM (2 mL), and the organic phase was separated and washed with water (2 mL) three times. The mixture was concentrated to dryness under reduced pressure at 40° C. to afford 250 mg of Compound A-Boc (tert-butyl 2-(4-bromophenyl)-3-((2-oxo-2-(quinolin-3-ylamino)ethyl)thio)-1,4,8-triazaspiro[4.5]deca-1,3-diene-8-carboxylate) with 85 A % LC purity in a 87% corrected yield.

Example 5: Synthesis of Compound A-Bn Via Steps (ii)(b) and (iii)

Compound I-H (3-(4-bromophenyl)-1,4,8-triazaspiro[4.5]dec-3-en-2-one) was synthesized according to the following reaction scheme:

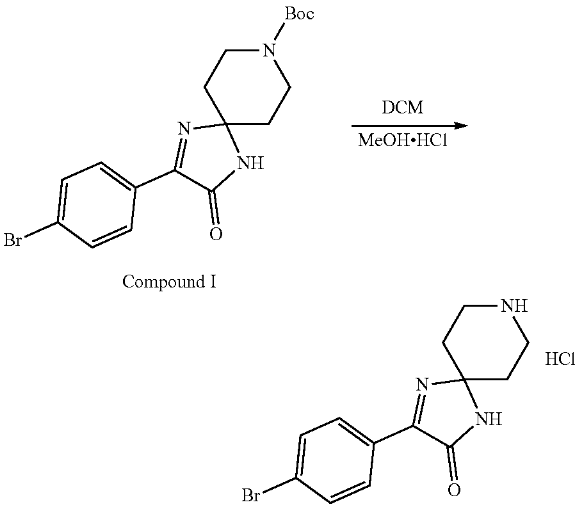

Compound I

Compound I-H

Compound I (tert-butyl 2-(4-bromophenyl)-3-oxo-1,4,8-triazaspiro[4.5]dec-1-ene-8-carboxylate, 55 g, 1.0 eq.) and DCM (2.7 L) were charged into a flask under $N_2$, and the solution was cooled to 0° C. To this solution was added HCl in MeOH (10 M, 115 mL, 10.0 eq.), and the mixture was warmed to 20 to 25° C. and stirred for 12 h. The mixture was filtered, and the filter cake was washed with DCM (110 mL). The filter cake was dried under reduced pressure at 40° C. for 6 h to afford 45 g of Compound I-H 3-(4-bromophenyl)-1,4,8-triazaspiro[4.5]dec-3-en-2-one with 94% LC purity in a 97% isolated yield.

Compound I-Bn (8-benzyl-3-(4-bromophenyl)-1,4,8-triazaspiro[4.5]dec-3-en-2-one) was synthesized according to the following reaction scheme:

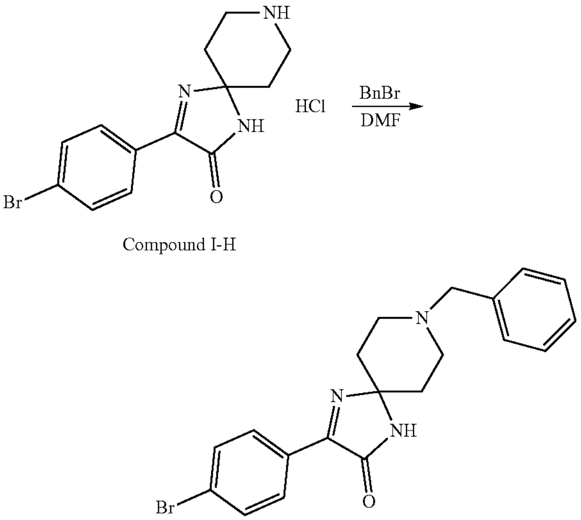

Compound I-H

Compound I-Bn

Compound I-H (3-(4-bromophenyl)-1,4,8-triazaspiro[4.5]dec-3-en-2-one, 45 g, 1.0 eq.), $Na_2CO_3$ (16.6 g, 1.2 eq.) and DMF (1.1 L, 25 v) were charged into a flask under $N_2$, and the solution was cooled to −5° C. To this solution was added benzyl bromide (26.8 g, 1.2 eq.), and the mixture was warmed to 20 to 25° C. and stirred for 2 h. To this mixture was added water (450 mL) and then EtOAc (450 mL). The organic phase was separated and washed with water (450 mL) two times, then concentrated to dryness under reduced pressure at 40° C. for 6 h to afford 48 g of Compound I-Bn 8-benzyl-3-(4-bromophenyl)-1,4,8-triazaspiro[4.5]dec-3-en-2-one with 94% LC purity in an 82% isolated yield.

Compound IIA-Bn (8-benzyl-3-(4-bromophenyl)-1,4,8-triazaspiro[4.5]dec-3-ene-2-thione) was synthesized according to the following reaction scheme:

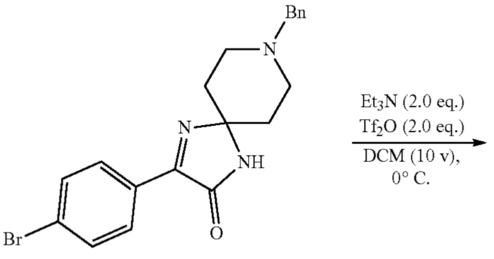

Compound I-Bn

-continued

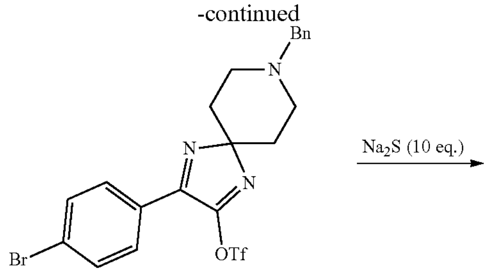

Compound II-Bn

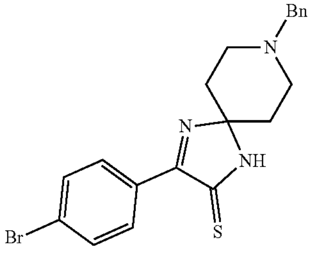

Compound IIA-Bn

Compound I-Bn (8-benzyl-3-(4-bromophenyl)-1,4,8-triazaspiro[4.5]dec-3-en-2-one, 500 mg, 1.0 eq.) and DCM (5 mL) were charged into a flask under $N_2$. To this solution was added $Et_3N$ (254 mg, 2.0 eq.), and the flask was purged with $N_2$ three times. The solution was cooled to 0° C., to this mixture was added a solution of $Tf_2O$ (528 mg, 2.0 eq.) in DCM (1 mL). This mixture was stirred at 0° C. for 1 h to yield Compound II-Bn (8-benzyl-3-(4-bromophenyl)-1,4,8-triazaspiro[4.5]deca-1,3-dien-2-yl trifluoromethanesulfonate) which was used directly in the next step without purification.

To the solution of Compound II-Bn from the previous step was added $Na_2S$ (1.96 g, 10.0 eq.), and the mixture was stirred at 0° C. for 1 h. To this solution was added water (5 mL) and then EtOAc (5 mL). The organic phase was separated and washed with water (5 mL) three times, then concentrated to dryness under reduced pressure at 40° C. This residue was purified by silica gel column chromatography (eluting with 2:1 (v/v) n-heptane/EtOAc) to give 210 mg of Compound IIA-Bn 8-benzyl-3-(4-bromophenyl)-1,4,8-triazaspiro[4.5]dec-3-ene-2-thione with 97 A % purity in a 40% yield from Compound I-Bn.

Compound A-Bn (2-((8-benzyl-3-(4-bromophenyl)-1,4,8-triazaspiro[4.5]deca-1,3-dien-2-yl)thio)-N-(quinolin-3-yl) acetamide) was synthesized according to the following reaction scheme:

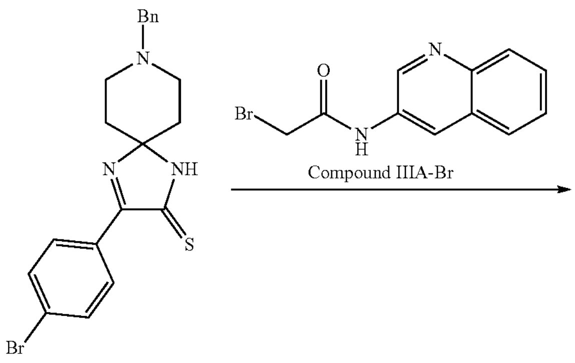

Compound IIIA-Br

Compound IIA-Bn

-continued

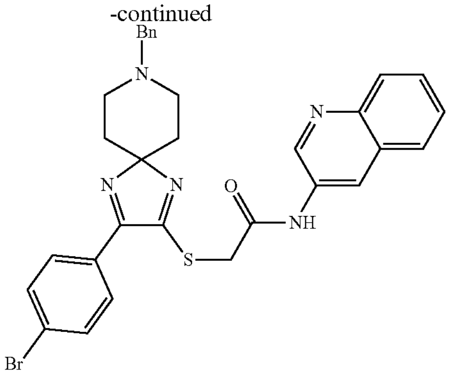

Compound A-Bn

Under an atmosphere of $N_2$, Compound IIA-Bn (8-benzyl-3-(4-bromophenyl)-1,4,8-triazaspiro[4.5]dec-3-ene-2-thione, 150 mg, 1.0 eq.) and DCM (1.5 mL) were charged into a flask and purged with $N_2$ three times. To this solution was added Compound IIIA-Br (101 mg, 1.05 eq) and $Et_3N$ (73 mg, 2.0 eq), and the solution was stirred at 20° C. for 5 h. To this mixture was added water (1.5 mL) and DCM (1.5 mL), and the organic phase was separated and washed with water (1.5 mL) three times. The mixture was concentrated to dryness under reduced pressure at 40° C. and purified by column chromatography (elute with 0-20% MeOH in DCM) to afford 0.1 g of Compound A-Bn (2-((8-benzyl-3-(4-bromophenyl)-1,4,8-triazaspiro[4.5]deca-1,3-dien-2-yl) thio)-N-(quinolin-3-Aacetamide) with 99% HPLC purity in a 46% corrected yield.

What is claimed is:

1. A process of synthesizing Compound A, or a salt thereof:

(Compound A)

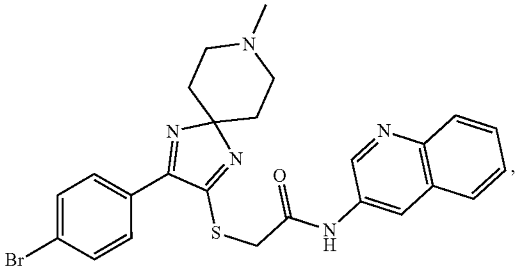

, comprising:

(i) admixing Compound I and a halogenation reagent or a sulfonylation reagent to form Compound II:

(I)

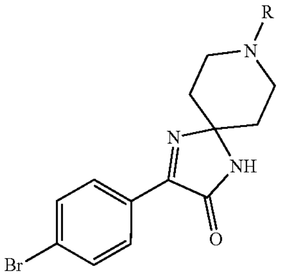

and

-continued (II)

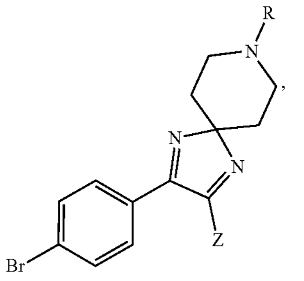

wherein R is methyl or a nitrogen-protecting group and Z is a halogen or a sulfonate group;

(ii)(a): if R is methyl, admixing Compound II and Compound III in the presence of a base to form Compound A:

(III)

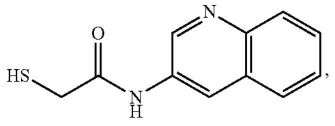

if R is a nitrogen-protecting group, admixing Compound II and Compound III in the presence of a base to form Compound IV:

(IV)

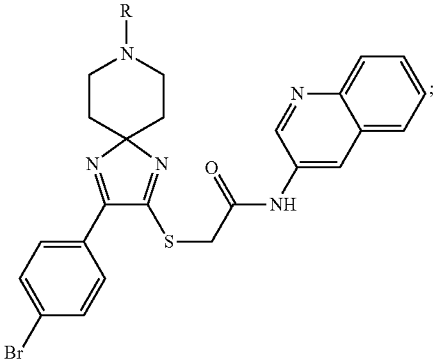

or (ii)(b): if R is methyl, (1) admixing Compound II and a nucleophilic sulfuration reagent to form Compound IIA, then (II) admixing Compound IIA with Compound IIIA in the presence of a base to form Compound A:

(IIA)

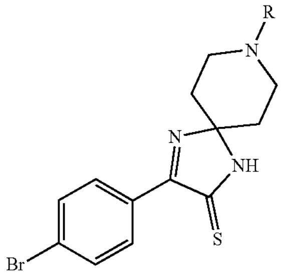

and (IIIA)

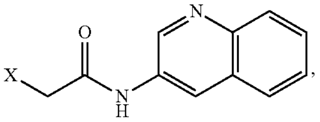

wherein X is halogen, or if R is a nitrogen-protecting group, (I) admixing Compound II and a nucleophilic sulfuration reagent to form Compound IIA, then (II) admixing Compound IIA with Compound IIIA in the presence of a base to form Compound IV; and (iii) when R is a nitrogen-protecting group, removing the nitrogen-protecting group from Compound IV and methylating the resulting deprotected amine to form Compound A.

2. The process of claim 1, wherein R is methyl.

3. The process of claim 1, wherein R is a nitrogen-protecting group.

4. The process of claim 1, wherein Z is halogen.

5. The process of claim 1, wherein the halogenation reagent is a chlorination reagent.

6. The process of claim 1, wherein Z is a sulfonate group.

7. The process of claim 6, wherein the sulfonate group is formed by treating Compound I with a sulfonylation reagent selected from triflic anhydride, mesyl chloride, mesic anhydride, tosyl chloride, tosic anhydride, nosyl chloride, and a perfluoroalkylsulfonic anhydride.

8. The process of claim 1, wherein X is Br or Cl.

9. The process of claim 1, comprising step (ii)(a).

10. The process of claim 9, wherein the base is NaH, NaOH, KOH, sodium methoxide, sodium ethoxide, sodium tert-butoxide, or potassium tert-butoxide.

11. The process of claim 1, comprising step (ii)(b).

12. The process of claim 11, wherein the nucleophilic sulfuration reagent comprises $Li_2S$, $Na_2S$, $K_2S$, $Li_2S_x$, $Na_2S_x$, $K_2S_x$, (wherein x=2-5), $NaBH_4/S$, NaSH, AcSK, thiourea or a salt or hydrate thereof.

13. The process of claim 11, comprising admixing Compound II with $Na_2S$ $4H_2O$ in a mixture of dichloromethane and ethyl acetate.

14. The process of claim 11, comprising admixing Compound IIA with Compound IIIA in the presence of $K_2CO_3$ to form Compound A.

15. The process of claim 14, wherein the step of admixing Compound IIA with Compound IIIA in the presence of $K_2CO_3$ to form Compound A is performed in isopropanol.

16. The process of claim 1, wherein R is a nitrogen-protecting group and the process comprises step (iii).

17. The process of claim 16, wherein step (iii) is performed between steps (ii)(b)(I) and (ii)(b)(II).

18. The process of claim 16, wherein removing the nitrogen-protecting group comprises admixing in the presence of acid.

19. The process of claim 16, wherein the deprotected amine is methylated by admixing with $NaBH(OAc)_3$, $CH_2O$, and acetic acid.

* * * * *